United States Patent
Barsne

(10) Patent No.: US 6,720,497 B1
(45) Date of Patent: Apr. 13, 2004

(54) ELECTRODE CABLE FOR ELECTRICAL STIMULATION

(75) Inventor: Måns Barsne, Stockholm (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/254,605
(22) PCT Filed: Sep. 3, 1997
(86) PCT No.: PCT/SE97/01470
§ 371 (c)(1),
(2), (4) Date: Jun. 8, 1999
(87) PCT Pub. No.: WO98/10826
PCT Pub. Date: Mar. 19, 1998

(65) Prior Publication Data
(65)

(30) Foreign Application Priority Data

Sep. 12, 1996 (SE) .................................... 9603318

(51) Int. Cl.⁷ .......................... H01B 7/18; H01B 9/02
(52) U.S. Cl. .................... 174/102 R; 174/103; 174/108
(58) Field of Search ..................... 174/102 R, 102 A, 174/106 R, 108, 119 R, 126.1, 126.2, 128.1; 607/116, 119, 122, 142; 600/373, 374, 375

(56) References Cited

U.S. PATENT DOCUMENTS

| | | | | |
|---|---|---|---|---|
| 4,559,951 A | * | 12/1985 | Dahl et al. ................ | 128/642 |
| 4,640,983 A | * | 2/1987 | Comte .................... | 174/119 R |
| 4,945,342 A | * | 7/1990 | Steinemann ............ | 174/113 R |
| 4,951,687 A | * | 8/1990 | Ufford et al. ............... | 128/786 |
| 5,246,014 A | * | 9/1993 | Williams et al. ............ | 607/122 |
| 5,360,442 A | * | 11/1994 | Dahl et al. .................. | 607/129 |
| 5,433,744 A | * | 7/1995 | Breyen et al. .............. | 607/125 |
| 5,456,705 A | * | 10/1995 | Morris ....................... | 607/119 |
| 5,483,022 A | * | 1/1996 | Mar ......................... | 174/128.1 |
| 5,522,875 A | * | 6/1996 | Gates et al. ................ | 607/127 |
| 5,609,622 A | * | 3/1997 | Soukup et al. ............. | 607/122 |
| 5,760,341 A | | 6/1998 | Laske et al. | |

FOREIGN PATENT DOCUMENTS

| | | |
|---|---|---|
| DE | OS 30 31 752 | 3/1981 |
| EP | 0 622 090 | 11/1994 |
| WO | WO 96/26674 | 9/1996 |

* cited by examiner

Primary Examiner—William H. Mayo, III
(74) Attorney, Agent, or Firm—Schiff Hardin LLP

(57) ABSTRACT

A medical electrode cable has an exterior, tubular insulating sheath containing a number of side-by-side wires arranged substantially parallel to the sheath and helically proceeding around and, along a longitudinal axis. At least one of the wires is a low-resistivity conductor, and at least two of the wires are high-resistivity conductors. All of the wires have equal diameters. The low-resistivity conductor is a wire having a core of a low-resistivity material encased in an exterior jacket of the same high-resistivity material which forms the high-resistivity conductors.

13 Claims, 1 Drawing Sheet

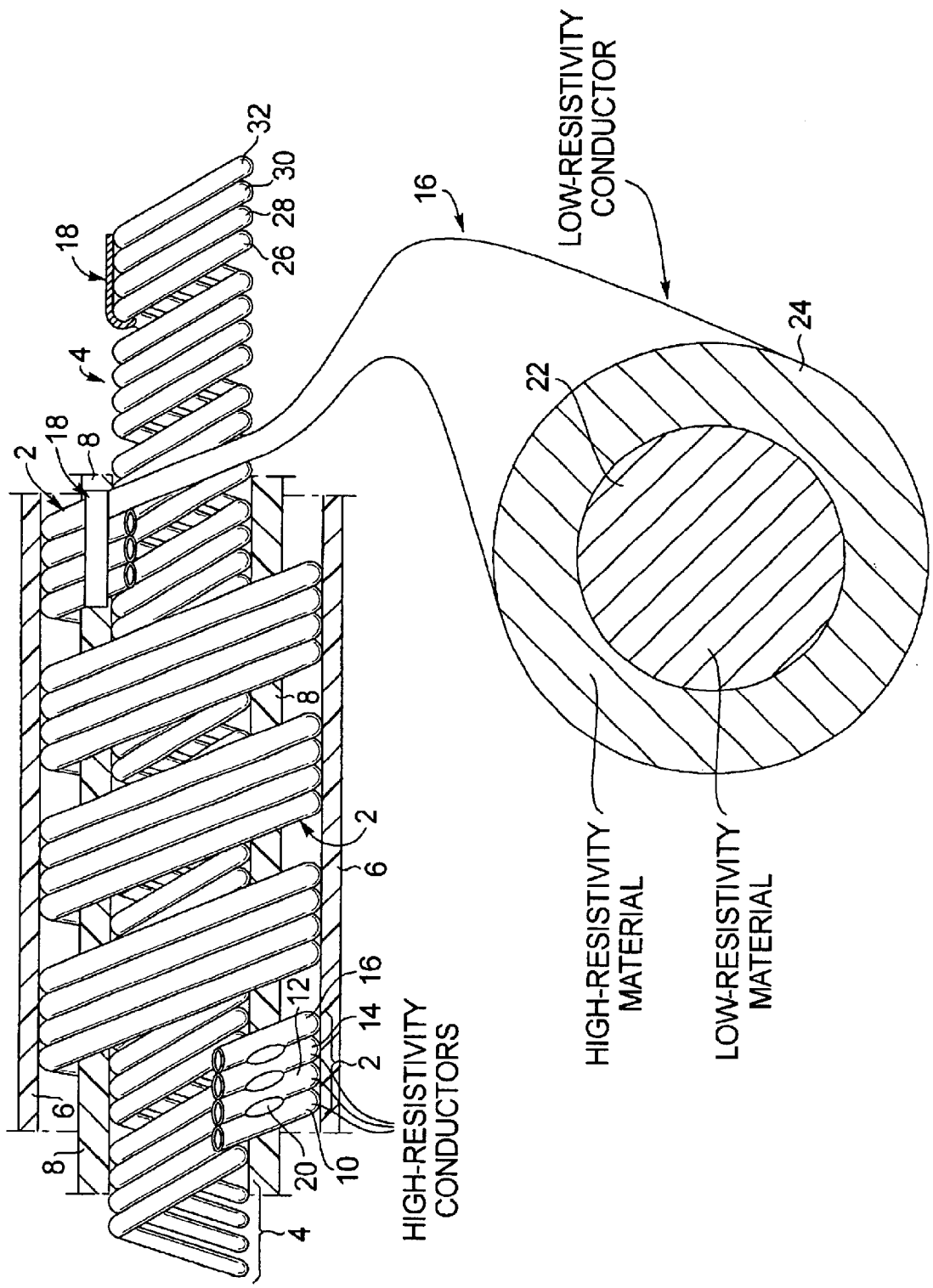

ELECTRODE CABLE FOR ELECTRICAL STIMULATION

BACKGROUND OF THE INVENTION

1. Field of the Invention

The present invention relates to an electrode cable of the type having a plurality of wires arranged helically along the length of the cable, said cable, which is encased in an outer, tubular sheath made of an electrically insulating material, suitable for use as an electrical connection between an electrical stimulation device, such as a heart stimulator, defibrillator etc. connectable to the proximal end of the cable, and an electrode connected to the distal end of the cable.

2. Description of the Prior Art

A lead device having one or more helices, each formed by at least one conductor, is known from European Application 0 162 178. Each conductor is formed by a number of wires arranged in a bundle by intertwining. All the wires in each conductor can be made of the same or of different materials. When different materials are used, the wires can differ in strength and electrical conductivity. This known lead device can be used as an electrical connection between e.g. a heart stimulator and contact electrodes for implantation in the human body. The objective of this known lead device is to achieve a device which, with the smallest possible external diameter for the helix, displays great fatigue resistance, relatively great electrical conductivity and small electrical resistance.

Each helical conductor in this known lead device has a core made of a wire and a plurality of wires coiled or wound around that core's longitudinal axis. The wires helically coiled around the core are intertwined into a bundle, making the lead device rather stiff and, therefore, scarcely suitable for advancement through the vascular system together with a stylet unit, inserted into a central channel in the lead device, to a desired location in the heart daring an implantation.

Another lead device having one or more helices that is similar to the above device is disclosed in U.S. Pat. No. 5,483,022. The difference is that each wire in the plurality of bundled wires is a wire having a conductive metal core jacketed in a sleeve of a less conductive metal having a higher strength and a better biocompatibility. One of the wires serves as a core similarly to the core in the above device.

SUMMARY OF THE INVENTION

An objective of the present invention is to provide a low-resistivity electrode cable which can be used as an efficient electrical connection between a device for electrical stimulation in the human body and an electrode connected to the device. The device can be e.g. a heart stimulator or defibrillator, and the electrode can be e g. an implantable heart electrode. The electrode cable can also be used for nerve stimulation. The electrode cable must be designed so it has very good electrical conductivity while simultaneously displaying optimal strength, tensile strength, flexural strength and fatigue resistance in particular.

In other words, the problem addressed by the invention is to provide an electrode cable with optimal properties in respect to its electrical conductivity, mechanical strength and ability to withstand dynamic stress capable of causing fatigue breakage of the cable, all of which are events which could have fatal consequences for a patient with a heart stimulator.

Another objective of the invention is to provide an electrode cable design making it possible to minimize the use of expensive materials in manufacturing the wires or conductors in the cable.

The problems cited in conjunction with the above objectives have conventionally been addressed to date by the use of either "high-resistivity" electrical conductors (>60Ω for a given reference length) or "low-resistivity" conductors (<15Ω for the same reference length) with a cylindrical spiral (helical) shape, a number of conductors wires (also referred to as wires) being helically wound or intertwined with each other.

In the use of such high-resistivity conductors, total resistance can obviously be reduced by e.g. increasing the total cross-sectional area of the conductive material in the lead, i.e. by increasing the near of wires in the lead and/or increasing the cross-section of each wire in the lead. However, an increase in the number of wires in the lead increases the lead's external diameter which is a disadvantage for a patient in whom such an electrode is to be implanted. The disadvantage is even greater if a plurality of leads must be implanted in the patient. However, an increase in the cross-sectional area of a conductor has an adverse impact on e.g. fatigue resistance. When the number of wires in a helical spiral increases, the pitch of each individual conductor wire also increases, thereby impairing the mechanical properties of the lead.

When the aforementioned type of low-resistivity conductors are utilized, the conductors employ wires made of either a low-resistivity material or a material which is a combination of a low-resistivity material and a high-resistivity material, the latter devised to carry the low-resistivity material. However, such low-resistivity wires have limiting mechanical properties.

The above objects are achieved in an electrode cable according to the invention containing at least a first set of electrically concussive wires, this first set of wires, (and each additional set of wires, if present) including at least one wire devised as a low-resistivity electrical conductor and at least two or three, wire(s) devised as (a) high-resistivity electrical conductor(s), and wherein all the low-resistivity and high-resistivity wires in each set of wires are conductors with the same diameter and are arranged side-by-side in a strip running parallel to the exterior of the cable sheath and extending helically along the cable's length. In a preferred embodiment all wires are conductors with the same diameter in the 0.05 to 0.20 mm range.

The following can be noted to clarify the concepts "low-resistivity" and "high-resistivity" wires (conductors) in the present application. These two concepts are designations whose primary purpose is to indicate that resistivities with clearly differing magnitudes are involved. The ratio between them is particularly important in this context. As is well-known, resistivity is an electrical ,unit measured in Ωm. The following are examples of magnitudes and ratios applicable to low-resistivity and high-resistivity wires respectively.

A example of a low- resistivity wire is a 5.8 m long wire with a cross-sectional area of 0.00785 mm$^2$ in which a low-resistivity material (silver) constitutes 28% of the conductive material and a high-resistivity material (MP35N) constitutes 72%. This results in a wire (conductor wire) with resistivity on the order of $5.4 \times 10^{-8}$ Ωm. A high-resistivity wire with the exact same geometry as the low-resistivity wire but made only of the high-resistivity material (MP35N) will have a resistivity on the order of about $2.5 \times 10^{-7}$ Ωm. The ratio between the resistivity of the high-resistivity wire and the low-resistivity wire according to this example will amount to about 4.6.

With this kind of hybrid helical wire spiral with one or two low-resistivity wires as the primary electrical conductor means, high-resistivity wires serving as secondary electrical conductor means, providing support for the low-resistivity wires and possessing good mechanical properties, a low-resistivity helical wire can be achieved, which also displays good mechanical properties.

In one preferred embodiment of the electrode cable according to the invention, wire connecting means are arranged on each cable end and accomplish electrical interconnection of all the wires in the respective wire set, thereby achieving their parallel connection in the cable. In this manner, a low-resistivity helical wire is obtained with good mechanical properties.

The wire connecting means on each cable end can e.g. be some appropriate type of metallic clamping means which achieve surface contact with each low-resistivity wire and one or more of the high-resistance wires. The clamping means can also be made of a pair of interacting parts which grip in/on the wire spiral. Alternately, the wire connecting means can consist of wire-connecting welded or soldered joints on the ends of the cable connecting the wires.

The high-resistivity wires in each wire set are conductors made of the same material, and the low-resistivity wire in each wire set is a wire conductor with a core of low-resistivity material (e.g. silver, gold, copper, platinum etc.), the core being encased in an external jacket made of the same kind of material as the material in the high-resistivity wires. The latter material could be e.g. a cobalt alloy such as MP35N or the like. Material in the external sheath of each low-resistivity wire comprises appropriately 65% to 80% of the wire's total volume. It has been shown that particularly good properties are achieved when the latter percentage amounts to about 72%.

With the invention, it also becomes possible to minimize the use (i.e. the required quantify) of a corrosible material (e.g. silver, copper etc.) in the electrode cable. The low-resistivity material risks becoming corroded or forming a cathode, the surrounding material becoming anodic, which may cause corrosion. In the electrode cable of the invention, the amount of mixed material can be reduced, thereby increasing the percentage of material such as MP35N, thus also improving the conditions for obtaining an effective welded joint.

The electrode cable according to the invention can be a unipolar cable, but the electrode cable can alternately contain additional electrical conductors (poles), the cable thus becoming bipolar or multipolar. An electrode cable devised as a bipolar cable according to the invention can contain a second set of helical wires forming the cable's second pole. In one embodiment, the inventive bipolar electrode cable is hollow throughout its length, having a longitudinal channel into which a stylet unit can be inserted. The stylet unit is temporarily inserted into the electrode cable during cable implantation to facilitate advancement of the cable through the vascular system to the desired location in the heart.

DESCRIPTION OF THE DRAWING

The single FIGURE is a schematic illustration of a short portion of an electrode cable in accordance with the invention, in longitudinal section, in the exemplary embodiment of a bipolar electrode cable.

DESCRIPTION OF THE PREFERRED EMBODIMENTS

The drawing shows a short section of a bipolar electrode cable according to the invention. This cable contains a pair of coaxially arranged, mutually insulated electrical conductors forming the cable's two poles at either end of the cable. Each of these two conductors, generally designated 2 and 4 respectively, is formed by four helically and cylindrically arranged wires, placed side-by-side, each wire of which constituting an electrical conductor. The outer conductor 2, as seen in the radial direction of the cable, is in this instance formed by a first set of electrically conductive wires 10, 12, 14 and 16. Of these four wires, the wire designated 16 is devised as a low-resistivity electrical conductor wire, whereas the wires 10, 12, 14 are all devised as high-resistivity electrical conductor wires providing lateral support for the low-resistivity wire 16 in addition to serving as conductors. As the drawing also shows, the cable is externally provided with a tubular sheath 6 made of an electrically insulating material, such a silicon rubber or polyurethane. A tubular sheath 8 made of an electrically insulating material is also arranged between the cable's two poles, i.e. between the first, outer set of wires, generally designated 2, and the inner set of wires, generally designated 4. As the drawing shows, the electrode cable is hollow throughout its length because the inner, second set of wires, generally designated 4, with its four helical wires, forms a longitudinal channel inside the cable. This longitudinal channel allows a stylet unit for cable maneuvering to be inserted into the interior of the electrode cable. The ability to maneuver the electrode cable is needed, in practice, when the cable is to serve as an electrical connection between a heart stimulator connectable to the proximal end of the cable, and an electrode on the distal end of the cable, which is to be advanced into a cavity of the heart and affixed to the cavity wall.

Wire connecting means are arranged on both cable ends (the proximal end and distal end respectively). Their task is to accomplish mutual electrical connection between all the wires in the respective wire sets so as to achieve parallel coupling of the wires in the respective wire set.

These wire connecting means on either end of the cable can be devised and arranged in different ways. In one conceivable embodiment, the wire connecting means consist of a U-shaped metallic clamping device 18 with two parallel jaws which achieve direct surface contact with the wires in a set of wires. A clamping device of this kind is schematically shown in a side view of the set 2 of wires and in a axial longitudinal section of the inner set of wires 4 (at the right end of the inner set 4 of wires). An alternative type of wire connection means at each end of the cable can consist of welded or soldered joints 20 between the wires in the set of wires. One such embodiment of the wire connecting means is shown to the left in the drawing at the end of the outer set 2 of wires.

As described above, the first, outer set 2 of wires is formed by the low-resistivity wire 16 and three high-resistivity wires 10, 12, 14. All four of the wires in this wire set consist of conductor wires with the same diameter in the 0.05 to 0.20 mm range. As the drawing shows, the wires 10, 12, 14 and 16 are located side-by-side in a strip, running "parallel" to the cable's external sheath 6 and extending helically along the length of the cable, located on the surface of an imaginary circular cylinder coaxial to the electrode cable's midline.

The three high-resistivity wires 10, 12, 14 in the set 2 of wires are conductor wires made of the same material, e.g. MP35N, and the only low-resistivity wire 16 in the set 2 of wires is a conductor wire with a core 22 made of a low-resistivity material, such as silver, as shown in a highly enlarged cross-section of the wire 16 at the bottom of the drawing. Here, the core 22 has a jacket 24 made of the same material as the material in the high-resistivity wires 10, 12, 14, i.e. MP35N in this instance.

The above-described construction according to he invention achieves the advantage that only one of the four wires in the set 2 of wires, viz the low-resistivity wire 16, is an expensive type with a core 22 of silver encased in a jacket 24 surrounding the core, made of the much cheaper cobalt alloy. All the other three of wires 10, 12, 14 in the set 2 of wires are also made of tie cheaper cobalt alloy, so the entire electrode cable is cheaper than if all the wires were of the same expensive type as the wire 16. All told, an electrode cable is achieved which is cheaper to make and in which expensive material is only used to optimize the cable's electrical conductivity, and cheaper material is used for the wires whose primary task is to give the cable the desired strength. The cheaper-to-make high-resistivity wires 10, 12, 14 have the double task of providing lateral support for the expensive low-resistivity wire 16 employed as the primary conductor, and serving as reserve (secondary) cable conductors if the low-resistivity wire or conductor 16 should break, e.g. due to a fatigue stress. This reserve function for the wires 10, 12, 14 is also the reason why they are made of an electrically conductive material, even though the material displays poorer conductivity than the material in the low-resistivity core 22 of the wire 16.

A hybrid type of helically wound electrode cable devised according to the invention and containing three high-resistivity wires and one low-resistivity wire can be expected to be 3–5 times more conductive than a geometrically identical, conventional, helically wound electrode cable.

As the above shows, the cable in the drawing, which is a bipolar cable, also has an inner, second set 4 of helical wires forming the cable's second pole, in addition to the first set 2 of wires serving as one of the cable's poles. The four wires in the second set 4 of wires are designated 26, 28, 30 and 32. These four wires can also be devised as a hybrid, i.e. only one of the wires in the inner set of wires 4 can be devised as a low-resistivity conductor containing an expensive material, whereas the other wires can be made of a material which gives the set of wires the desired strength. As the above shows, certain other properties of an electrode cable according to the invention are also important, in addition to heir electrical properties, and therefore merit special attention. As regards the cable's fatigue resistance and flexibility, the ratios s/D and d/D (where s=pitch, D=external diameter and d=the diameter of wire in the wire helix) are especially important parameters. Some examples of typical ratios in this context and strength values are given below.

Fatigue

For a spiral conductor to survive millions of bendings, as an electrode cable must do in vivo, s/D and d/D must be as small as possible. The value s/D=1.0 is a large value, whereas s/D=0.1 is a small value. The value d/D=0.5 is very large, whereas d/D<0.1 is small.

EXAMPLE 1

A spiral conductor, made of the material MP35N, with four wires has the ratio d/D=0.0875 and s/D=0.4. If this spiral conductor is bent with a radius of 6 mm, an effective stress (von Mise's) amounting to about 320 MPa is obtained.

EXAMPLE 2

A spiral conductor (MP35N) with d/D=0.0875 and s/D=0.1, bent with a radius of 6 mm, gives an effective stress of about 75 MPa.

EXAMPLE 3

A spiral conductor (MP35N) with d/D=0.218 and s/D=1.0, bent with a radius of 6 mm, gives an effective stress of about 1050 MPa.

The material MP35N has a breaking point at about 1850 MPa and a yield point of about 1250 MPa at a 0.2% offset.

Flexibility

Both the ratio s/D and d/D must be as small as possible if the spiral is to be very flexible. This cannot be achieved in practice with traditional conductors made of MP35N without resistance rising to an excessively high level.

Tensile strength

Tensile strength obviously declines with a declining cross-sectional area for all the wires in a spiral conductor. When a wire has a filled core (e.g. a silver filling), tensile strength declines in the spiral, which is undesirable. When a hybrid spiral according to the invention with only one silver-filled wire is used, strength and resistance are optimized compared to the use of three or four wires filled with silver.

Although modifications and changes may be suggested by those skilled in the art, it is the intention of the inventor to embody within the patent warranted hereon all changes and modifications as reasonably and properly come within the scope of his contribution to the art.

I claim:

1. A medical electrode cable having a longitudinal axis, comprising:
   an exterior, tubular insulating sheath;
   a plurality of wires disposed side-by-side substantially parallel to said sheath and forming a wire set, said wire set extending helically around and along said longitudinal axis;
   one of said plurality of wires in said wire set consisting of a low-resistive conductor;
   at least two of said plurality of wires in said wire set respectively consisting of high-resistive conductors, each of said high-resistive conductors consisting of a same high-resistivity material;
   all wires in said plurality of wires having equal respective diameters; and
   said low-resistive conductor being a wire consisting of a core exclusively of a low-resistivity material encased in an exterior jacket exclusively of said high-resistivity material.

2. A medical electrode cable as claimed in claim 1 having a first end adapted for connection to a medical electrical stimulation device, and a second end having an electrode for delivering stimulation energy from said medical stimulation device, said stimulation energy being conducted through said medical electrode cable by said wire set.

3. A medical electrode cable as claimed in claim 1 wherein said wire set has a first end and a second end, and further comprising a first wire connector disposed at said first end and a second wire connector disposed at said second end, said first and second wire connectors each establishing an electrical connection among all of said plurality of wires in said wire set.

4. A medical electrode cable as claimed in claim 3 wherein each of said first and second wire connectors comprise a metallic clamp disposed in direct surface contact with said low-resistive conductor and at least one of said high-resistive conductors.

5. A medical electrode cable as claimed in claim 3 wherein each of said first and second wire connectors comprise a plurality of joints electrically connecting side-by-side wires in said wire set, said joints being selected from the group consisting of soldered joints and welded joints.

6. A medical electrode cable as claimed in claim 1 wherein said high-resistivity material comprises a cobalt alloy, and wherein said low-resistivity material comprises a material selected from the group consisting of silver, gold, aluminum, copper and platinum.

7. A medical electrode cable as claimed in claim 6 wherein said low-resistive conductor has a total conductor volume, and wherein said outer jacket of said low-resistivity conductor comprises a portion of said total conductor volume in a range between 65% and 80%.

8. A medical electrode cable as claimed in claim 1 wherein said wire set encompasses a hollow interior extending entirely along said longitudinal axis.

9. A medical electrode cable as claimed in claim 8 wherein said plurality of wires comprise a first plurality of wires and wherein said wire set comprises a first wire set, said medical electrode cable further comprising:

an interior, tubular insulating sheath disposed in said interior volume and extending along said longitudinal axis; and a second plurality of wires disposed side-by-side substantially parallel to and inside said interior sheath, said second plurality of wires forming a second wire set extending helically around and along said longitudinal axis coaxially with said first wire set.

10. A medical electrode cable as claimed in claim 9 wherein said second wire set also includes one wire comprising a low-resistive conductor and at least two wires comprising respective high-resistive conductors, with each of the high-resistive conductors in said second wire set being comprised of said high-resistivity material and said low-resistive conductor in said second wire set having a core of said low-resistivity material encased in an exterior jacket comprised of said high-resistivity material.

11. A medical electrode cable as claimed in claim 10 wherein said second wire set has a hollow interior proceeding entirely along said longitudinal axis forming a channel having a size adapted to admit a stylet unit.

12. A medical electrode cable as claimed in claim 9 wherein each wire in said first plurality of wires forming said first wire set and each wire in said second plurality of wires forming said second wire set has a diameter in a range between 0.05 and 0.20 mm.

13. A medical electrode cable as claimed in claim 1 wherein each wire in said plurality of wires forming said wire set has a diameter in a range between 0.05 and 0.20 mm.

* * * * *